United States Patent
Schofield

(10) Patent No.: US 10,049,767 B2
(45) Date of Patent: Aug. 14, 2018

(54) TEST PANEL TO MEASURE BLOOD NEUROTOXIN LEVELS IN PREMATERNAL WOMEN AND FOR THE GENERAL PUBLIC IN RELATION TO MENTAL DISORDERS OF THE AGING

(71) Applicant: Keith Schofield, Santa Barbara, CA (US)

(72) Inventor: Keith Schofield, Santa Barbara, CA (US)

( * ) Notice: Subject to any disclaimer, the term of this patent is extended or adjusted under 35 U.S.C. 154(b) by 0 days.

(21) Appl. No.: 15/840,699

(22) Filed: Dec. 13, 2017

(65) Prior Publication Data

US 2018/0166154 A1  Jun. 14, 2018

Related U.S. Application Data

(62) Division of application No. 15/379,352, filed on Dec. 14, 2016.

(51) Int. Cl.
| | | |
|---|---|---|
| *H01J 49/00* | (2006.01) | |
| *G16H 10/40* | (2018.01) | |
| *G01N 33/49* | (2006.01) | |
| *H01J 49/10* | (2006.01) | |

(52) U.S. Cl.
CPC .......... *G16H 10/40* (2018.01); *G01N 33/492* (2013.01); *H01J 49/0027* (2013.01); *H01J 49/105* (2013.01)

(58) Field of Classification Search
None
See application file for complete search history.

(56) References Cited

U.S. PATENT DOCUMENTS

| | | | | |
|---|---|---|---|---|
| 2003/0203495 A1* | 10/2003 | Rupp | ..................... | G01N 31/22 436/74 |
| 2006/0104827 A1* | 5/2006 | Shaw | ...................... | G01N 1/38 417/245 |
| 2006/0127237 A1* | 6/2006 | Shaw | ...................... | G01N 1/38 417/313 |
| 2008/0202196 A1* | 8/2008 | Richardson | ............ | A62B 27/00 73/1.06 |

(Continued)

FOREIGN PATENT DOCUMENTS

WO    WO 2016034600 A1 * 3/2016 ......... G01N 33/6893

*Primary Examiner* — Andrew Smyth
(74) *Attorney, Agent, or Firm* — Marcus C. Dawes; Daniel L. Dawes

(57) ABSTRACT

A prescribed diagnostic blood test panel is directed to countering autistic and mentally affected births and assessing the continued healthy mental state of the elderly. Six neurotoxins in the blood are analyzed, five of which can produce damage to the brain, namely aluminum, arsenic, lead, mercury and manganese. The sixth, selenium, although a toxin at high levels is in fact a protective element for the brain within a certain concentration range providing important cleansing mechanisms for the alien neurotoxins. This test establishes a baseline set of values for these six neurotoxins and provides guidance for preventive measures to minimize potential risk of neurological consequences. This reduces the risk of autism in new births and is especially valuable to the general public in providing a tool to possibly avoid the consequences of diseases in old age such as dementia, Parkinson's or Alzheimer's.

8 Claims, 1 Drawing Sheet

(56) References Cited

U.S. PATENT DOCUMENTS

| | | | |
|---|---|---|---|
| 2008/0261207 A1* | 10/2008 | Mitsuhashi | C12Q 1/6886 435/6.14 |
| 2015/0147276 A1* | 5/2015 | Ingber | A61K 41/0014 424/9.5 |
| 2015/0251991 A1* | 9/2015 | Jay | C07C 229/16 514/547 |
| 2015/0335281 A1* | 11/2015 | Scroggins | A61B 5/4869 600/410 |
| 2017/0285049 A1* | 10/2017 | Schatz | G01N 33/92 |

* cited by examiner

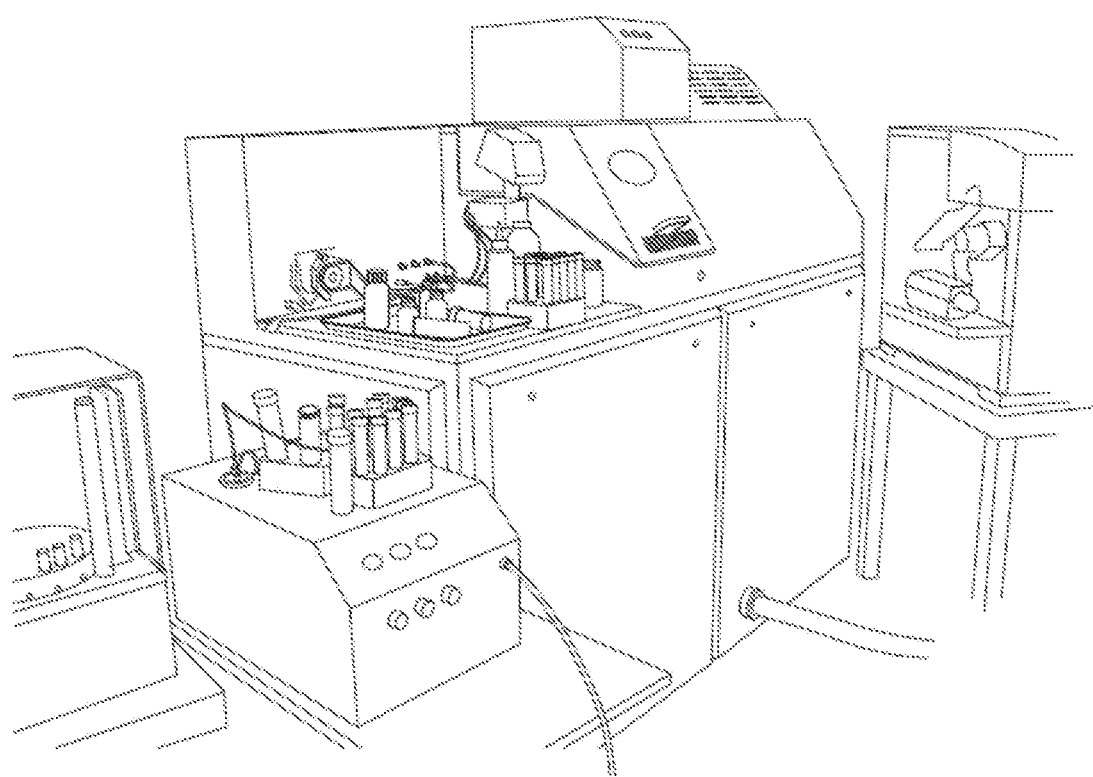

TEST PANEL TO MEASURE BLOOD NEUROTOXIN LEVELS IN PREMATERNAL WOMEN AND FOR THE GENERAL PUBLIC IN RELATION TO MENTAL DISORDERS OF THE AGING

RELATED APPLICATIONS

The present application is a divisional of U.S. application Ser. No. 15/379,352, filed on Dec. 14, 2016, which is incorporated herein by reference and to which priority is claimed pursuant to 35 USC 120.

BACKGROUND

Field of the Technology

The invention relates to the field of medical treatments by providing a simply prescribed diagnostic test panel for a patient's blood sample as a preventive measure to counter autistic and mentally affected births and for assessing the continued healthy mental state of the elderly.

Description of the Prior Art

The aim of the medical profession is to maintain as high a quality of health in the general populace as possible. Until recent years its predominant emphasis has been on diagnosing illnesses and providing cures. Without symptoms there has been an assumption of health with less emphasis placed on preventive care. However, there is a growing concern that modern lifestyles and the ever changing environment in which we live may be the root cause of various syndromes and mental aberrations that previously rare are now becoming commonplace.

Autism in the US now has a rate of one in eighty births whereas 30-40 years ago it was one in ten-thousand. The nature of mental disorders in children appears to cover a wide spectral range and the age related deteriorations that similarly have a range of names such as dementia, Parkinson's or Alzheimer's have impacted many people. Such illnesses are no longer thought to be mainly coupled to genetic aspects, but are in fact a consequence of the environment. The medical profession at present is in a quandary concerning such situations as no cures are available.

Medical research now has been proceeding for many years to try and identify causes, but prematernal women thinking of pregnancy face great stress and worry which is difficult for doctors to relieve. Seemingly healthy pregnant women are giving birth to autistic children. The same anguish applies to families with aging adults when they see no guarantee that a deterioration in mental ability will not strike the elderly.

In life, decisions are invariably made for a reason or need. For example, the airport is constantly serviced with planes that are readily available. Nevertheless, they are never used unless people have a reason for a flight. This now is the situation in medicine, instrumentation has been around now for a decade or more that will analyze people's blood. However, if people appear healthy a doctor will not consider any analyses, when there is no apparent reason, other than those now standardized such as blood pressure, lipid panel (cholesterol) etc. They rarely do exploratory testing since the body is too complex. However, one reason is now clear with the growing epidemic of mental illness, but there are no simple procedures presently suggested and no standardized testing particularly for prematernal women who need an assurance of their body's health in this respect. National Survey studies have clearly shown that all women have specific baseline values of neurotoxins in their blood yet appear perfectly healthy. It fully depends on their living environment and their lifestyle. These are beyond a doctor's knowledge. Consequently for any women about to become pregnant such baseline values remain unknown but are precious information. If known it would enable time to permit a lowering of neurotoxins which not only safeguards a fetus but undoubtedly also enhance the body's ability to counter any other underlying systemic infections that may not be apparent. Hopefully the introduction of such a simple test panel will begin a process of aimed at reducing neurological illnesses.

What is needed is a method to provide doctors with the information to not only remove some of this the present concern especially for future mothers, but also to provide the tool where each person can know the state of their body throughout life relating to any concerns about potential neurological damage. At present this is not readily available and if considered in a random manner is applied only in part too late. What is needed is a blood test panel that emphasizes the potential for minimization of mental disorders that result from possible neurotoxin damage specifically to the brain.

BRIEF SUMMARY

The illustrated embodiments of the invention include a method for assessing neurotoxic risk levels in a subject. The method includes the steps of: measuring a blood baseline value in the subject of the six metallic neurotoxins encountered in the body that are comprised of aluminum, arsenic, mercury, lead and manganese, together with selenium; comparing the measured baseline values of the six neurotoxins, including aluminum, arsenic, mercury, lead, manganese, and selenium against corresponding known minimum risk level (MRL) values of these six neurotoxins, to determine risk of neurotoxic effects; and diagnosing the risk of potential neurological diseases that include autism in a fetus, or dementia, Parkinson's or Alzheimer's diseases in an adult.

The step of measuring a blood baseline value in the subject of the six neurotoxins and comparing the measured baseline values against a known standard minimum risk level for an elderly subject or a prematernal woman.

The step of measuring a blood baseline value in the subject of the six neurotoxins includes measuring a blood baseline value in the subject of the six neurotoxins with an inductively coupled plasma mass spectrometric analyzer.

The step of measuring a blood baseline value in the subject of the six neurotoxins includes measuring a blood baseline value in the subject of the six neurotoxins by atomic absorption spectroscopy, thermal ionization mass spectrometry or glow discharge mass spectrometry, or any correspondingly adequate analyzer that may become available.

The method further includes adjusting the expected average minimum risk level (MRL) values according to the subject's gender and body weight.

The method step of measuring a blood baseline value in the subject of six neurotoxins, namely, aluminum, arsenic, mercury, lead, manganese, and selenium includes simultaneously measuring on one analytical system a set of blood baseline values in the subject of these six neurotoxins.

The step of comparing the measured baseline values of the six neurotoxins, including aluminum, arsenic, mercury, lead and manganese, together with selenium and assessing the degree of risk of neurotoxic effects of the six neurotoxins, including aluminum, arsenic, mercury, lead, manganese, and selenium to diagnose any potential disease state by comparison with standardized minimum risk levels. This will provide a doctor with the necessary information to prescribe suggested changes in diet or lifestyle to reduce this risk to an accepted level.

The step of assessing the risk of neurotoxic effect of the six neurotoxins, including aluminum, arsenic, mercury, lead, manganese, and selenium to diagnose the level of risk and over time monitor the patient. This then minimizes any continuation of an unhealthy bodily state and further facilitates the ability for additional corrective measures.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112.

BRIEF DESCRIPTION OF THE DRAWINGS

FIG. 1 is a photograph of a conventional fully functioning inductively coupled plasma-mass spectrometer capable of quantitatively analyzing simultaneously the six neurotoxin elements in a blood sample according to the invention.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

The illustrated embodiments of the invention are particularly directed to the detection and effect of neurotoxins. The human brain is mainly protected by the blood-brain barrier (BBB). This is a network of tightly knit cells whose purpose is to shut out from the brain any alien species in the body, only allowing necessary nutrients to enter. It is very effective and the reason there has been difficulty in devising drugs to treat the brain is that the drugs simply cannot enter. Unfortunately, there are certain elements and their compounds that by various means, such as having small molecular size or being organic in nature, disguise their nature and manage to overcome this obstacle. In particular these are the six known neurotoxins addressed in this patent and are known for having the ability to enter and damage the brain. They differ in this way from normal toxins or poisons that are excluded from the brain. The body generally can control these, utilizing the kidneys and liver or if in excess with the additional aid of medical chelation. The brain does have its own additional protection in containing chelating or self-cleansing proteins and enzymes. These detoxing molecules, now often referred to as anti-oxidants, generally contain sulfur or selenium and can be effective at sequestering a neurotoxin and gradually removing it. However, this is not an instant process and from animal studies the brain half-life of each of the neurotoxins has been estimated and can be measured in days or more. How long the neurotoxins are active in the brain to inflict damage before being nullified remains uncertain. Also, the extent by which the brain can repair itself to some degree if abused remains uncertain. As a result, even for the healthiest, the body has a constant burden that is continuous from birth until death removing body toxins. Moreover, we are totally dependent on the brain defense mechanisms and their efficiencies and constant operation. We normally accept this and assume the functions are trouble free. For many, who are fortunate, this does appear to be the case. In reality it is not really known whether brain defenses are occasionally stretched too much and we have no simple way of asking that question at present other than seeing a consequence.

Although the world now has millions of chemicals in circulation, many of which are obnoxious and toxic, we are in a way fortunate that the number of generally encountered neurotoxins with which humans interface is only a handful. These are mainly the elements and compounds of aluminum (Al), arsenic (As), mercury (Hg), lead (Pb) and manganese (Mn). These are all alien to the body, serving no purpose except for manganese that does play numerous roles and as a consequence may self-regulate its concentration to some degree in the body and as a result is of lesser concern. Selenium differs from the others in that although a neurotoxin above a certain dose it is vital to the brain being involved in the brain's protective mechanisms. Whether we like it or not, it can be very difficult for the average person to avoid these elements in life. As indicated in the Table below, these neurotoxins are encountered in food, water and even dust particles besides other sources. However, with knowledge we would have an enhanced ability to minimize them and their effects.

Aluminum as its hydroxide has replaced mercury (thimerosal) in many domestically US consumed vaccines. Although not normally regarded as dangerous by the medical profession, this assumption was only based on orally consumed data. In fact a toxicology assessment suggested a high value minimum risk level of 1.0 mg Al/kg body weight/day. However, such digested aluminum has only a 1% absorption by the intestines whereas intravenous injection from a vaccine is a totally different consideration as it is 100% absorbed in the blood. More recent critical reviews have indicated the risk factor of this and connected it with autism and Alzheimer's disease. Brain uptake, retention in adults and aluminum loading in preterm neonates also has been extensively reported. In the manufacturing of infant foods, there is still pronounced concerns about the aluminum content in the product. As listed by the Mayo Clinic and the Micro Trace Minerals diagnostic centers and portrayed in the Table below they now recommend an MRL of <6 microgram/liter for blood content.

Arsenic is well known as a historical murder poison and in certain districts can be a contaminant of the drinking water, possibly its major source for many people. Its toxicology is well documented. Although found in fish, this is mainly as an organic form (arsenobetaine) only mildly toxic, not digested and

TABLE 1

Neurotoxin testing for blood levels, measured in microgram per liter units.

| Neurotoxin | US National Survey Results | | Minimum Risk Level | Dietary and Other Sources |
| --- | --- | --- | --- | --- |
| | Range | Average | | |
| Aluminum | 3.8-17 | 4.6 | <6 | Vaccines, food (cereals, nuts), water |
| Arsenic | 2.6-8.5 | 4.0 | <10 | Seafood (minor), poultry, water, low in most foods |
| Lead | 3-38 | 18 | <50 | Old plumbing, paint, leaded glass, water, air dust, low in foods |
| Manganese | 1.6-63 | 9.2 | <18 | Teas, food (nuts, bread, cereal, fruit), air dust, water |
| Mercury | 0.2-33 | 0.8 | <2-9 | Vaccines, seafood (Sushi), dentistry |
| Selenium | 144-253 | 190 | <70-130 | Food (nuts, eggs, fish), water | excreted without being metabolized. However, it is one element that can methylate in the body. In other words it can change if it is ingested in an inorganic structure to one that is organic and becomes a more potent neurotoxin.

Mercury is a more dangerous neurotoxin particularly in modern times. It has been shown that inorganic mercury such as in tooth amalgam does have trouble getting through the BBB. However, its organic forms as thimerosal still used to various extents in vaccines (metabolizing in the body to ethyl mercury), and the mercury in all fish as the methylated organic form (methyl mercury) have been monitored in fetal birth cords, and in brain autopsies of fetus, babies and seniors. Experiments on monkeys in particular have clearly illustrated the passage of organic mercury into the brain, its half-life and behavior. One important difference with organic mercury is that the easy influx can modify once in the brain (demethylation or de-ethylation) and revert to an inorganic form that then is more difficult to egress. The high risk associated with mercury is becoming very evident by an increased level of mercury poisonings being noted by the medical profession. This is a recent change with which they were not previously familiar. It appears to arise from the recent strong upturn in eating fish Sushi style.

There now is an overwhelming number of animal studies with all these neurotoxins in the medical literature. This includes lead which in various ways may have contributed to the downfall of Rome. The recent contamination of drinking water in Flint Mich. again has highlighted the heavy dependency on trusting the safety of what we eat and drink. Lead is a potent neurotoxin and much more easily absorbed by children and so will certainly have consequences for that population. However, it still remains of general concern as it was used in lead/silver solder for welding copper water piping and was used in oil paints. As a result it remains in our environment in all older houses, although now banned, as was also leaded gasoline and leaded cut glass. It remains a problem in the US but is even more evident in other countries with high values recently evident in the public of Norway and seen in the perinatal levels of mothers in Austria.

Manganese differs from these other neurotoxins in being necessary to the body. Although extensively studied with animals, only tentative dietary suggestions of about 10 mg/day for an average man have been suggested. A survey of 7720 US citizens arrived at an average blood content value of 9.2 microgram/liter in blood with only slightly higher levels in women. However, as seen in the attached table, the measured range of values in that survey stretched from 1.6 to 63 microgram/liter indicating that some of those tested (called the outliers) had levels that were much higher for this element, the consequences remaining unknown. Manganese is also documented to cross the blood brain barrier as the other four mentioned and can affect fetal normal behavior. All these neurotoxins are evident in all human blood and that of pregnant women. However, small levels do appear needed in the case of manganese.

The body is seen to be highly complex and even for these neurotoxins it has innumerable proteins and enzymes that provide protection for the brain. One very important element in this regard is selenium and current studies have clearly identified this even though larger doses of this can in fact also be toxic. Many animal studies have been reported but a relevant one clearly indicated that if selenium was fed to rats at a similar atomic quantity as these neurotoxins, neural damage could be minimized and was apparently negligible. Also studies have shown that selenium is beneficial to human conception and pregnancy and when given to the elderly as a supplement has shown noticeable neural improvements. As a result, there is now a huge field of medical studies that have remained uncoordinated but they do indicate that better patient monitoring would be invaluable. Also, it is clear that neurotoxins are potentially hazardous during pregnancies and also may accumulate in the brain in various ways throughout life. Keeping them at low levels has to be immensely beneficial. There is a general feeling among some in medical research that the safe level for any neurotoxin is zero. All the medical studies that have been reported to establish databases of average values for the general public or for pregnant women do indicate the ever presence of these neurotoxins in the blood of everybody coupled to other poisonous species, poisonous to the body but not the brain. With all these neurotoxins similar distributions have been noted that can cover a broad range of values, some people obviously having better body control mechanisms and some having greater retentions. It is the neurotoxins that can damage the brain. As seen from the Table, in those people tested in the US, numerous exceeded the minimum risk level particularly for aluminum, manganese and mercury and would be of concern in some cases if pregnant. The above average values for selenium seen in the US population are undoubtedly of benefit. In countries with poor selenium bearing soils low values for selenium would enhance risk concerns with the other neurotoxin ranges.

In recent decades a minor explosion has occurred in science concerning the analytical ability for monitoring. In spite of this, the medical profession remains lax at monitoring the baseline of these neurotoxins in individuals or prematernal women. Moreover it remains very difficult for them to authorize such a test and invariably this is not undertaken. A disastrous scandal occurred in Minamata, Japan, 60 years ago concerning toxic mercury contamination of the adjacent lake. This resulted in many birth defects but surprisingly showed no effect on the mothers. This remains the problem, the mother being an adult can handle certain levels of neurotoxins because her brain is fully formed. The fetus though is far more vulnerable in that it is not only small but its brain is in early stages of development. It survives in the majority of cases by its own brain defense mechanisms. The number of birth miscarriages is globally high, with signs of being on the increase, and generally happens in the very early stages of development often before the woman realizes she is pregnant. This emphasizes more so the importance of testing prematernal women before they become pregnant. In addition, the effects of a neurotoxin generally tend to have been studied singly. There is very little discussion of synergistic effects and it is quite possible that the sum of the neurotoxic levels in the body may be collaboratively more dangerous.

The illustrated embodiments of the invention include a test profile that can simultaneously analyze a blood sample for these six elements. This can be achieved on an inductively coupled plasma mass spectrometric analyzer that is now available globally and can be programmed to do such a task. Inductively coupled plasma mass spectrometry (ICP-MS) is a type of mass spectrometry which is capable of detecting the presently discussed metals at concentrations as low as ten parts in a trillion (I in $10^{11}$), two orders of magnitude more sensitive than the parts per billion scale required in the proposed blood analyses (micrograms per liter). The disclosure can be better visualized by turning now to a photograph of the monitoring device, see FIG. 1 that would be used in a diagnostic testing facility. It is not a large instrument but fully computerized and now generally available and reliably standardized particularly in regard to measuring these six elements. It can be readily operated by a trained technician. This is achieved by aspirating the blood or calibration sample at a fixed and constant rate into a high temperature (5000° C.) argon plasma that almost fully atomizes and ionizes the metallic content of the sample. This plasma then enters a mass spectrometer that resolves the elemental ions into a highly dispersed mass spectrum and quantifies their intensities. These are scaled absolutely by utilizing calibration samples containing known levels of the species of interest. At these concentration levels the response is linear, making calibration easy. Moreover, the system has now been proven valid for these six elements, possible interferences from the argon gas carrier observed for arsenic and selenium have been resolved by utilizing alternate interference free isotopic lines that exist for these. Moreover such an instrument normally is very stable during a day and only infrequent validation calibration is needed. Such instruments are fully automated and computerized such that a sample enters the system and the results are printed out. With a qualified technician the results can be very accurate (±10%). In the present test panel this is much more than needed. For a doctor or patient the general magnitude is all that is necessary and a ±50% result would be satisfactory.

At present, compared to other analytical methods the ICP-MS has greater speed, precision, and sensitivity. However, any future instrument development that is comparable or superior can also readily be used to produce the needed test panel results.

The disclosed blood panel is a simple test panel that a doctor can readily request on a prescription. It will provide blood analysis values to compare with the prescribed minimum risk levels suggested by the various toxicology services that includes the World Health Organization in Geneva. Such results can readily be studied by the recipient to identify any sources that may be resulting in any observed elevated levels. The body has always been able to handle certain loads but overloading could be easily avoided. This would be valuable for anyone that wishes to question their body and live with this knowledge rather than being totally uncertain. People who enjoy fish are totally surprised when they are suddenly diagnosed with mercury poisoning. This test panel of elements is not currently available from medical diagnostic analytical laboratories. It is not readily obtained, but in fact is not difficult to implement in any advanced analytical laboratory. Such a test panel would be an invaluable medical advance undoubtedly capable of saving many lives and providing a simple resource that would facilitate less emotional concern for anyone in such need.

People live their lives without really knowing the state of their bodies. Often living is a learning experience when people risk abusing the body to gauge its limits. Currently, the best example of this is the eating of fish. Fish is nutritious and fits the description of a healthy and delicious food. However, more and more people are being diagnosed as having mercury poisoning. Pregnant women are in a predicament when they are told by their doctor to try and balance the risk against the benefit of fish in their diet. A simple blood test can provide an effective diagnostic tool, particularly for the six neurotoxins evident in everybody's blood, aluminum, arsenic, mercury, lead and manganese, together with the important antioxidant selenium. These can all be measured simultaneously on one analytical system, or in other ways if preferred, using a single standard blood sample quantity. The results can be readily compared with recommended average safe values. An individual then has the necessary information to assess the nature of these values, and if decided take measures to minimize them to lower levels. They are all neurotoxins and should all be measured, it is not sufficient to examine only one. It is highly probable that they have collaborative or cumulative effects in the brain.

In summary, the illustrated embodiments of the invention relates to the medical profession by providing a simply prescribed diagnostic test panel for a patient's blood sample. It is a preventive measure to counter the current epidemic of autistic and mentally affected births and will be equally valuable for assessing the continued healthy mental state of the elderly. It involves analyzing the six neurotoxins in the blood, five of which can produce damage to the brain, namely aluminum, arsenic, lead, mercury and manganese. The sixth, selenium, although a toxin at high levels is in fact a protective element for the brain within a certain concentration range providing important cleansing mechanisms for the alien neurotoxins. From toxicology, the minimum risk levels for these are known but a general consensus now is that minimum risk levels for five of them should be as close to zero as is possible. With modern life styles this is not evident and everybody has these toxins in their blood to a variety of degrees. This simple test establishes a baseline set of values for these six neurotoxins. This then provides instant guidance for a doctor and the individual for preventive measures to minimize potential risk of neurological consequences. This is of paramount importance for women before pregnancy to reduce the risk of autism and is especially valuable to the general public in providing a tool to possibly avoid the consequences of diseases in old age such as dementia, Parkinson's or Alzheimer's. With modern technology this procedure can be readily put in place such that this panel of neurotoxin levels could be trivially prescribed for by a simple single blood test. Currently, this is not in the domain of obstetrician/gynecologists or general practitioner's testing protocols in any manner and remains difficult for them to prescribe specifically for these six neurotoxins.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

I claim:

1. A method for assessing risk for developing a neurological disease in a subject comprising:
   measuring a blood baseline value in the subject of six neurotoxins including aluminum, arsenic, mercury, lead and manganese, together with selenium;
   generating calibrated concentrations of the six neurotoxins from their measured baseline values;
   comparing the calibrated concentrations of the six neurotoxins, including aluminum, arsenic, mercury, lead and manganese, together with selenium with corresponding expected average minimum risk level (MRL) values of the six neurotoxins, including aluminum, arsenic, mercury, lead and manganese, together with selenium to determine the degree of risk of neurotoxic effects;
   assessing the risk of neurotoxic effects of the six neurotoxins, including aluminum, arsenic, mercury, lead and manganese, together with selenium to minimize the possibilities of neurological diseases; and
   automatically generating a report of calibrated concentrations of the six neurotoxins,
   wherein measuring the blood baseline value comprises:
      aspirating a blood sample into a high temperature argon plasma that atomizes and ionizes any metallic content of the blood sample; and
      simultaneously analyzing the blood sample for a defined metallic content of the six neurotoxins including aluminum, arsenic, mercury, lead, manganese, and selenium in the plasma in a mass spectrometer by resolving the elements into a highly dispersed mass spectrum to quantify their intensities.

2. The method of claim 1 where assessing the risk of neurotoxic effects of the six neurotoxins, including aluminum, arsenic, mercury, lead and manganese, together with selenium to minimize the possibilities of neurological diseases comprises assessing the risk of autism damage to a fetus, the occurrence of dementia, Parkinson's or Alzheimer's diseases.

3. The method of claim 1 where measuring a blood baseline value in the subject of the six neurotoxins and comparing the calibrated concentrations with the expected average minimum risk level includes measuring a blood baseline value and comparing the calibrated concentrations with such a standard for an elderly subject or a prematernal woman.

4. The method of claim 1 where measuring a blood baseline value in the subject of the six neurotoxins includes measuring a blood baseline value in the subject of the six neurotoxins with an inductively coupled plasma mass spectrometric analyzer.

5. The method of claim 1 where measuring a blood baseline value in the subject of the six neurotoxins includes measuring a blood baseline value in the subject of the six neurotoxins by mass spectroscopy or other analyzer.

6. The method of claim 1 further comprising adjusting the expected average minimum risk level (MRL) values according to the subject's gender and body weight.

7. The method of claim 1 where comparing the calibrated concentrations of the six neurotoxins, including namely aluminum, arsenic, mercury, lead and manganese, together with selenium assesses the risk of neurotoxic effects of the six neurotoxins in connection with potential neurological diseases.

8. The method of claim 7 where assessing the risk of neurotoxic effect of the six neurotoxins, namely aluminum, arsenic, mercury, lead and manganese, together with selenium is compared to prior test results of an individual to monitor any change in the degree of risk concerning various potential neurological illnesses and enable subsequent procedures to be suggested.

* * * * *